United States Patent
Wada et al.

(10) Patent No.: US 10,294,162 B2
(45) Date of Patent: May 21, 2019

(54) DETONATION-MEDIATED CARBON PARTICLE PRODUCTION METHOD

(71) Applicants: KOBE STEEL, LTD., Hyogo (JP); NATIONAL INSTITUTE OF ADVANCED INDUSTRIAL SCIENCE AND TECHNOLOGY, Tokyo (JP)

(72) Inventors: Ryutaro Wada, Tokyo (JP); Masaya Ueda, Hyogo (JP); Yozo Kakudate, Ibaraki (JP); Shuzo Fujiwara, Ibaraki (JP); Shu Usuba, Ibaraki (JP)

(73) Assignees: KOBE STEEL, LTD., Hyogo (JP); NATIONAL INSTITUTE OF ADVANCED SCIENCE AND TECHNOLOGY, Tokyo (JP)

(*) Notice: Subject to any disclaimer, the term of this patent is extended or adjusted under 35 U.S.C. 154(b) by 1 day.

(21) Appl. No.: 15/107,840

(22) PCT Filed: Dec. 24, 2014

(86) PCT No.: PCT/JP2014/084182
§ 371 (c)(1),
(2) Date: Jun. 23, 2016

(87) PCT Pub. No.: WO2015/098982
PCT Pub. Date: Jul. 2, 2015

(65) Prior Publication Data
US 2016/0318809 A1 Nov. 3, 2016

(30) Foreign Application Priority Data
Dec. 27, 2013 (JP) .................. 2013-273468

(51) Int. Cl.
*C01B 31/02* (2006.01)
*C04B 35/52* (2006.01)
*B01J 3/08* (2006.01)
*A61K 47/06* (2006.01)
*C04B 35/64* (2006.01)
*C01B 32/05* (2017.01)
*C01B 32/20* (2017.01)
*C01B 32/25* (2017.01)

(52) U.S. Cl.
CPC ............ *C04B 35/522* (2013.01); *A61K 47/06* (2013.01); *B01J 3/08* (2013.01); *C01B 32/05* (2017.08); *C01B 32/20* (2017.08); *C01B 32/25* (2017.08); *C04B 35/64* (2013.01); *C04B 2235/425* (2013.01); *C04B 2235/427* (2013.01)

(58) Field of Classification Search
CPC .................................................. C01B 32/05
See application file for complete search history.

(56) References Cited

U.S. PATENT DOCUMENTS

| 4,483,836 | A | 11/1984 | Adadurov et al. |
|---|---|---|---|
| 8,227,685 | B2* | 7/2012 | Choi ............... B82Y 30/00 136/252 |
| 2003/0228249 | A1 | 12/2003 | Fujimura et al. |
| 2006/0147644 | A1 | 7/2006 | Fujimura et al. |
| 2009/0285744 | A1 | 11/2009 | Sugihara et al. |
| 2010/0069513 | A1 | 3/2010 | Fujimura et al. |
| 2011/0209642 | A1 | 9/2011 | Fujimura et al. |

FOREIGN PATENT DOCUMENTS

| JP | 2005-289677 A | 10/2005 |
|---|---|---|
| JP | 4245310 B2 | 3/2009 |
| JP | 2011-037693 A | 2/2011 |
| JP | 2012-135718 A | 7/2012 |
| JP | 2012-170913 A | 9/2012 |
| JP | 2012-193106 A | 10/2012 |
| JP | 2013-056805 A | 3/2013 |
| JP | 5155975 B2 | 3/2013 |

OTHER PUBLICATIONS

Pichot et al., 'An Efficient Purification Method for Detonation Nanodiamonds' in Diamond & Related Materials vol. 17 pp. 13-22 (2008).*
T. Komatsu et al., "Balloon-shaped graphitic-carbon material induced by shock-compression of dehydrochlorinated poly(vinylidene chloride)," J. Mater. Chem., vol. 8, No. 12, Dec. 1, 1988, pp. 2725-2728.
N. Kozu et al., "Shock and Static Compression of Nitrobenzene," Jpn. J. Appl. Phys., vol. 39, No. 8, Part 1, Aug. 2000, pp. 4875-4880.
Extended European Search Report (EESR) dated Aug. 2, 2017, from corresponding EP Appl No. 14875584.6, 7 pp.
Youzou Kakudate; "2-3. Dynamic High Pressure (Detonation Method)"; Handbook of Diamond Technology; Industrial Diamond Association of Japan, NGT, Jan. 2007; pp. 28-33; Japan; with English language translation.
A.E. Aleksenskii et al.; "Effect of Hydrogen on the Structure of Ultradisperse Diamond"; Physics of Solid State; 2000; pp. 1575-1578; vol. 42; No. 8; Russia.
International Search Report; PCT/JP2014/084182 dated Mar. 3, 2015; with English language translation.
Written Opinion of the International Searching Authority; PCT/JP2014/084182 dated Mar. 3, 2015; with English language translation.

* cited by examiner

*Primary Examiner* — Stuart L Hendrickson
(74) *Attorney, Agent, or Firm* — Studebaker & Brackett PC

(57) ABSTRACT

A method for producing a carbon particle by a detonation method includes two steps. The first step is a step of disposing an explosive substance in the periphery of a raw material substance. The explosive substance has a detonation velocity of 6,300 m/s or more. The raw material substance contains an aromatic compound having not more than 2 nitro groups. The second step is a step of allowing the explosive substance to detonate.

12 Claims, 3 Drawing Sheets

DETONATION-MEDIATED CARBON PARTICLE PRODUCTION METHOD

TECHNICAL FIELD

The present invention relates to a method for producing carbon particles by a detonation method. In more detail, the present invention relates to a method for producing carbon particles containing graphite carbon and diamond by a detonation method that uses a raw material substance containing an aromatic compound having not more than 2 nitro groups (hereinafter referred to as "non-low explosive raw material").

BACKGROUND ART

Nano-scale diamond (hereinafter referred to as "nanodiamond") has a large number of excellent properties such as a high hardness and an extremely low coefficient of friction, and therefore, it has been already utilized in various fields and its development of application has been investigated as an extremely promising new material.

It is known that nanodiamond can be, for example, synthesized by utilizing a detonation reaction of a high explosive. This synthesis method is one named a detonation method, in which a detonation is performed with only a raw material substance containing an aromatic compound having 3 or more nitro groups as a carbon source (hereinafter referred to as "low explosive raw material"), and a carbon atom decomposed and liberated, by the detonation reaction, from a molecule constituting the low explosive raw material is formed as diamond at high temperature and high pressure during the detonation (see, for example, NPL 1).

A production of nanodiamond by the detonation method has hitherto been performed in, for example, the East European countries inclusive of Russia and the Ukraine, the United States of America, China, and the like. In these countries, since a military waste low explosive is inexpensively available as the low explosive raw material that is a carbon source, trinitrotoluene (TNT), a high explosive mixture of TNT with hexogen (RDX: trimethylenetrinitramine) or octogen (HMX: cyclotetramethylenetetranitramine), and the like have been used. In the present invention, the high explosive refers to a material capable of performing the detonation reaction, and the low explosive raw material and the non-low explosive raw material are included in the high explosive. In addition, an explosive substance refers to a substance capable of causing an abrupt combustion reaction and includes a substance that is solid at normal temperature and normal pressure and a substance that is liquid at normal temperature and normal pressure; however, the term refers to a solid explosive substance that does not have fluidity at normal temperature and normal pressure unless otherwise indicated in the present specification.

It is anticipated that the demanded amount of the nanodiamond will increase more and more in the future following the development of its application. However, as for the production using a military waste low explosive, there is a limit in the production volume. Therefore, there is a possibility that the supply will be short in the international market in the future. Then the domestic production is expected but, according to an advance evaluation made by the present inventors, it has become clear that, in general, the above-described low explosive raw material is expensive and hence, the production costs become high, leading to unprofitability in economy.

Now, the nanodiamond produced by the detonation method contains carbon impurities mainly composed of nano-scale graphite carbon (hereinafter referred to as "nanographite") that is a carbon fraction not having a diamond structure.

Hitherto, it has been considered that the carbon impurities are an undesirable existence in utilizing excellent properties of the nanodiamond. Therefore, in conventional techniques, it has been focused to prepare the nanodiamond by removing carbon impurities such as nanographite, as far as possible through various purification methods or chemical treatments (see, for example, PTLs 1 and 2). However, the nanographite has different physical properties such as low hardness and high electroconductivity as compared with the nanodiamond, and in addition, it has such characteristic features that it is able to be bound to a large amount of heterogeneous atom other than carbon, or a functional group, so that it can be given a new function. Therefore, attention is paid to the nanographite as a promise novel material capable of being given various properties through single use thereof or as a mixture with nanodiamond.

CITATION LIST

Patent Literature

PTL 1: Japanese Patent No. 4245310
PTL 2: Japanese Patent No. 5155975

Non-Patent Literature

NPL 1: Yozo Kakudate (author), "2.3 Dynamic High Pressure (Detonation Method)", Industrial Diamond Association of Japan (compiler), "Diamond Technology Overview", NGT, January 2007, pp. 28-33

SUMMARY OF INVENTION

Technical Problem

An object of the present invention is to provide a method capable of producing carbon particles containing nano-scale graphite carbon and diamond by a detonation method that uses a non-low explosive raw material which is inexpensive and capable of being stably supplied.

Solution to Problem

The present inventors have found that carbon particles obtained by a detonation method using a non-low explosive raw material are a novel carbon material containing nano-scale graphite carbon and diamond (hereinafter referred to as "carbon particles"), leading to accomplishment of the present invention.

The nanodiamond or nanographite is formed in a manner that a raw material substance causes detonation to be decomposed to an atomic level and a carbon atom liberated therefrom without being oxidized aggregates in a solid state. During detonation, the raw material substance is in a high-temperature high-pressure state due to a decomposition reaction; however, it is immediately expanded and cooled. A process from this high-temperature high-pressure state to the reduced-pressure cooling is caused within a very short time as compared with usual combustion or deflagration that is an explosion phenomenon slower than detonation, and hence, there is no time when the aggregated carbon largely grows, whereby the nano-scale carbon particles are formed. In the case where a typical high-performance high explosive (for example, a high explosive mixture of TNT and RDX) which is known to cause detonation is used as the raw material substance, the pressure during the detonation becomes very high, and hence, as is easily anticipated from a thermodynamic equilibrium phase diagram of carbon, the formed carbon particles contain a lot of diamond (nanodiamond). In consequence, in order to efficiently produce carbon particles having a large proportion of nanographite, it is important to choose a raw material substance having a composition in which not only the pressure during detonation is an appropriate value, which is lower than that in a high-performance high-explosive, but also the liberated carbon is not oxidized.

In addition, the requirement that the pressure during detonation of the raw material substance is lower than that in a high-performance high explosive means a possibility of occurrence of a phenomenon in which it may be difficult to detonate the raw material substance, or even if detonation can be performed, it may be interrupted on the way. Therefore, it is necessary to contrive to dispose an explosive substance capable of causing detonation in the periphery of the raw material substance, thereby allowing the raw material substance to stably cause detonation, as described below.

That is, the present invention is to provide a method for producing a carbon particle by a detonation method, which includes using a raw material substance containing an aromatic compound having not more than 2 nitro groups and disposing an explosive substance having a detonation velocity of 6,300 m/s or more in the periphery of the raw material substance, thereby allowing the explosive substance to stably detonate.

In the production method of the present invention, the raw material substance preferably contains at least one non-low explosive raw material selected from the group consisting of dinitrotoluene, dinitrobenzene and dinitroxylene. The explosive substance may be a liquid having fluidity at a normal temperature and a normal pressure (hereinafter referred to as "liquid high explosive"). As compared with the case of using a solid explosive substance, when the liquid high explosive is used, a degree of freedom of shape is high, an increase in size is easy, and the operability or safety may be enhanced. The explosive substance may also be an explosive substance in which carbon is not included as a constituent element. In addition, the above-described liquid (liquid high explosive) may also be one containing at least one kind selected from the group consisting of a mixture of hydrazine and hydrazine nitrate, a mixture of hydrazine and ammonium nitrate, nitromethane, and a mixture of hydrazine and nitromethane.

In the production method of the present invention, it is preferred to perform the detonation in a state where the raw material substance and the explosive substance are charged within a chamber, and/or in a state where a coolant is disposed in the periphery of the raw material substance and the explosive substance within the chamber. Here, so far as an atmosphere within the chamber does not contain an oxygen gas, and/or so far as the coolant is a substance which does not substantially produce an oxidative substance such as oxygen and ozone, an oxidation reaction may be inhibited, and hence, a proportion in terms of a mass ratio, at which the carbon particle may be recovered from carbon in the raw material substance (specifically a "yield" that is a mass ratio of the carbon particle relative to the raw material substance) may be enhanced.

The production method of the present invention may further include a step of recovering the carbon particle from a residue obtained in the above-described detonation step. In this recover step, for example, if a classification/purification treatment is performed, the carbon particle may be obtained in a form of powder having a desired particle diameter. Arbitrary two or more of these respective preferred embodiments may be combined.

In addition, the present invention provides a carbon particle obtained by the above-described production method. This carbon particle contains a graphite carbon and a diamond and is high in the content proportion of the graphite carbon as compared with conventional products (the case of using a low explosive raw material).

Advantageous Effects of the Invention

In accordance with the present invention, it is possible to cause stable detonation by a detonation method that uses an inexpensive non-low explosive raw material and to produce carbon particles containing graphite carbon and diamond. In addition, it is possible to obtain carbon particles containing a lot of graphite carbon and having different surface properties, as compared with the conventional products using a low explosive raw material.

DESCRIPTION OF EMBODIMENTS

<<Production Method of Carbon Particles>>

Figure 1:
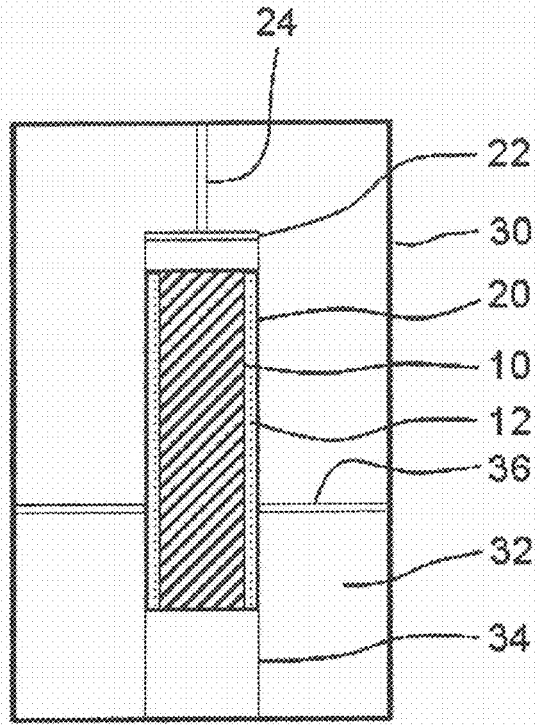
FIG. 1 is a cross-sectional view schematically illustrating an example of an explosive device which is used for the production method of the present invention.

The production method of the present invention is concerned with a method for producing carbon particles containing graphite carbon and diamond by a detonation method, the method including a step of disposing an explosive substance having a detonation velocity of 6,300 m/s or more in the periphery of a raw material substance containing an aromatic compound having not more than 2 nitro groups and a step of detonating the explosive substance.

In the production method of the present invention, first of all, an explosive substance having a detonation velocity of 6,300 m/s or more is disposed in the periphery of a raw material substance containing an aromatic compound having not more than 2 nitro groups. The aromatic compound having not more than 2 nitro groups is a non-low explosive raw material contained in the raw material substance that is a carbon source for the detonation method. The explosive substance having a detonation velocity of 6,300 m/s or more is a substance capable of causing stable detonation in order to form carbon particles from the raw material substance. In the case where a molecule constituting the explosive substance contains a carbon atom, the explosive substance may possibly work as a carbon source together with the raw material substance.

The aromatic compound having not more than 2 nitro groups is a compound having a structure in which 0, 1 or 2 hydrogen atoms of an aromatic ring, such as benzene, naphthalene or anthracene, are substituted with a nitro group. The aromatic compound may have other substituent than the nitro group. Examples of such a substituent include an alkyl group, a hydroxyl group, a hydroxyalkyl group, an amino group, and a halogen group. Though there may be the case where position isomers are present depending upon a positional relation of the nitro group or substituent, it is possible to use all of those position isomers in the production method of the present invention. For example, in the case where the aromatic compound is nitrotoluene, position isomers thereof are three kinds inclusive of 2-, 3- and 4-nitrotoluene. Examples of the above-described aromatic compound include benzene, toluene, xylene, naphthalene, anthracene, nitrobenzene, nitrotoluene, nitroxylene, nitronaphthalene, nitroanthracene, dinitrobenzene, dinitrotoluene, dinitroxylene, dinitronaphthalene, and dinitroanthracene. Among these aromatic compounds, dinitrotoluene (DNT), dinitrobenzene (DNB), dinitroxylene (DNX), and the like are preferred because they are easily available, and are easily moldable due to their low melting points. The aromatic compound may be used solely or may be used in combination of two or more kinds.

The raw material substance may further contain, in addition to the aromatic compound having not more than 2 nitro groups that is the non-low explosive raw material, a low explosive raw material. The low explosive raw material is, for example, a compound having 3 or more nitro groups and in general, is a nitro compound which is subjected to an application for explosion. Examples of the nitro compound include trinitrotoluene (TNT), hexogen (RDX: trimethylenetrinitramine), octogen (HMX: cyclotetramethylenetetranitramine), pentaerythritol tetranitrate (PETN), and tetryl (tetranitromethylaniline). The nitro compound may be used solely or may be used in combination of two or more kinds.

A content proportion of the aromatic compound having not more than 2 nitro groups in the raw material substance is generally 50 mass % or more, preferably 80 mass % or more, more preferably 90 mass % or more, and still more preferably 95 mass or more relative to a total mass of the raw material substance. When the aromatic compound having not more than 2 nitro groups that is an inexpensive non-low explosive raw material is contained in a high proportion, the content proportion of the compound having 3 or more nitro groups that is an expensive low explosive raw material may be decreased, and hence, the content proportion of the aromatic compound having not more than 2 nitro groups has an upper limit of most preferably 100 mass %. The upper limit may preferably be 99 mass % or about 98 mass %.

The detonation velocity of the explosive substance to be disposed in the periphery is required to be made higher than the detonation velocity of the raw material substance. For example, though it is difficult to stably detonate DNT (true density: 1.52 g/cm$^3$, melting point: 67 to 70° C.) that is an example of the raw material substance, the detonation velocity in the case where it can be detonated is anticipated to be about 6,000 m/s. For that reason, the detonation velocity of the explosive substance must be made to be more than this. Therefore, in the present invention, the detonation velocity of the explosive substance is prescribed to be 6,300 m/s or more. A detonation velocity of representative explosive substances is generally 10,000 m/s or less. In consequence, the detonation velocity of the explosive substance in the present invention may be prescribed to be 10,000 m/s or less. The detonation velocity is a propagation velocity of detonation in the case where the explosive substance causes detonation and is measured by the Dautriche method, the ion gap method, the optical fiber method, or the like. As for the detonation velocity prescribed in the present invention, reference is made herein to LASL Explosive Properties Data, ed. Gibbs. T. R. and Propolato, A., University of California Press, Berkeley, Los Angeles, London, 1980. In addition, as for the detonation velocity of DNT, reference is made herein to Combustion and Flames, Vol. 14 (1970), p. 145. As for the detonation velocity of nitromethane, reference is made herein to Kusakabe and Fujiwara, "Studies regarding Detonation of Liquid High Explosives (First Report)", Journal of the Industrial Explosives Society, Japan, Vol. 40, No. 2 (1979), p. 109. As for the detonation velocity of NH+HH (hydrazine nitrate ($H_2N$—$NH_2$.$HNO_3$) and hydrazine hydrate ($H_2N$—$NH_2$.$H_2O$)), reference is made herein to Kusakabe, et al., "Studies regarding Detonation of Liquid High Explosives (Third Report)", Journal of the Industrial Explosives Society, Japan, Vol. 41, No. 1 (1980), p. 23. The detonation velocity of representative explosive substances is shown in the following Table 1. As the explosive substances in Table 1, substances capable of being stably detonated are shown.

TABLE 1

| Explosive Substance | Molecular Formula | Density [1] (g/cm$^3$) | Detonation Velocity (m/s) | Melting Point (° C.) |
|---|---|---|---|---|
| TNT | $C_7H_5N_3O_6$ | 1.64 | 6940 | 80.9 |
| RDX | $C_3H_6N_6O_6$ | 1.77 | 8640 | 204.1 |
| HMX | $C_4H_8N_8O_8$ | 1.89 | 9110 | 278.0 |
| PETN | $C_5H_8N_4O_{12}$ | 1.67 | 7980 | 142.9 |
| Tetryl | $C_7H_5N_8O_8$ | 1.68 | 7670 | 129.4 |
| Composition B [2] | — | 1.71 | 8020 | 80.1 |
| Octol (75/25) [3] | — | 1.81 | 8450 | 80.1 |
| Nitromethane | $CH_3NO_2$ | 1.13 | 6260 | — |
| NH + HH [4] | — | 1.39 | 8330 | — |

[1] Density during detonation velocity measurement
[2] Composition B is a high explosive mixture of 59.5 wt % of RDX, 39.5 wt % of TNT and 1.0 wt % of a wax.
[3] Octol is a high explosive mixture of 75 wt % of HMX and 25 wt % of TNT.
[4] Hydrazine-based liquid high explosive obtained by mixing hydrazine nitrate ($H_2N$—$NH_2$•$HNO_3$) and hydrazine hydrate ($H_2N$—$NH_2$•$H_2O$) in a mass ratio of 3:1

Examples of the explosive substance include TNT, RDX, HMX, PETN, tetryl, a high explosive mixture composed mainly of RDX and TNT (for example, Composition B), and a high explosive mixture composed mainly of HMX and TNT (for example, Octol).

A liquid high explosive may also be used as the explosive substance. As compared with the case of using a solid, when a liquid is used as the explosive substance, a degree of freedom of shape is high, an increase in size is easy, and the operability or safety may be enhanced. Examples of the liquid high explosive include a mixture of hydrazine (inclusive of a hydrate thereof, i.e. hydrazine hydrate) and hydrazine nitrate, a mixture of hydrazine and ammonium nitrate, a mixture of hydrazine, hydrazine nitrate and ammonium nitrate, nitromethane, and a mixture of hydrazine and nitromethane.

Among the above-described explosive substances, one as a solid-state is preferably TNT which is easy for molding because of low melting point, or Composition B containing TNT as a mail component, or the like. The explosive substance may be used solely or may be used in combination of two or more kinds. Properties of representative explosive substances are shown in the foregoing Table 1.

A use amount of each of the raw material substance and the explosive substance may be properly adjusted according to the desired amount of carbon particles and is not particularly limited. A ratio thereof (explosive substance/raw material substance) is preferably 0.1 or more and more preferably 0.2 or more, and is preferably 1 or less, more preferably 0.9 or less and still more preferably 0.8 or less, in terms of a mass ratio. When the use amount ratio is less than 0.1, since a sufficient detonation reaction for forming carbon particles may not be performed, the yield is possibly decreased. Conversely, when the use amount ratio is more than 1, since the explosive substance is used more than necessary, the production costs possibly increase.

A mode for carrying out the production method of the present invention is hereunder described in detail by reference to the accompanying drawings. FIG. 1 is a cross-sectional view schematically illustrating an example of an explosive device which is used for the production method of the present invention. The explosive device illustrated in FIG. 1 is merely an exemplification, but it does not intend to limit the present invention thereto.

First of all, an explosive substance 12 is disposed in the periphery of a raw material substance 10. On the occasion of disposing the explosive substance 12 in the periphery of the raw material substance 10, it is preferred to symmetrically dispose the raw material substance 10 and the explosive substance 12 such that high temperature and high pressure following a shock wave generated by detonation of the explosive substance 12 are uniformly applied to the raw material substance 10 as far as possible, namely such that the symmetry of explosion shape is guaranteed. Then, for example, in the case where all of the raw material substance 10 and the explosive substance 12 urea solid, a molded body in a concentric columnar shape may be prepared by, for example, melt loading or pressed loading the raw material substance 10 and the explosive substance 12 in a cylindrical slit mold. In the case where the raw material substance 10 is a solid and the explosive substance 12 is a liquid high explosive, there may be adopted a method in which a columnar molded body is prepared by, for example, melt loading or pressed loading the raw material substance 10, and the molded body is placed in the center of the inside of a cylindrical container while allowing the axial direction to agree therewith, followed by injecting the liquid high explosive in the periphery thereof. In the case where the raw material substance 10 is a liquid and the explosive substance 12 is a solid, there may be adopted a method in which a concentric hollow columnar molded body is prepared by, for example, melt loading or pressed loading the explosive substance 12, followed by injecting the raw material substance 10 in a hollow part thereof. A container 20 housing the raw material substance 10 and the explosive substance 12 therein is hereinafter referred to as "explosion container". As the explosion container 20, it is preferred to use a container made of a synthetic resin, for example, an acrylic resin, etc., because it is possible to prevent contamination with impurities such as metals.

In the production method of the present invention, subsequently, the explosive substance 12 is detonated to form carbon particles from the raw material substance 10. A shock wave generated by a detonation reaction of the explosive substance 12 propagates towards the raw material substance 10, the raw material substance 10 is compressed by this shock wave to cause detonation, and a carbon atom decomposed and liberated from an organic molecule constituting the raw material substance 10 changes to carbon particles containing nanographite carbon and nanodiamond.

Though the detonation may be performed in either an open system or a closed system, it is preferred to perform it in a closed system, for example, in a state where the raw material substance and the explosive substance are charged within, for example, a metal-made chamber (for example, in a state where a molded body of the raw material substance and the explosive substance, or an explosion container having the raw material substance and the explosive substance housed therein, is suspended within a chamber), because a scattering of a residue in a wide area can be inhibited. The chamber which is used for performing the detonation is hereinafter referred to as "explosion chamber". On the occasion of detonation, so far as the atmosphere within the explosion chamber does not substantially contain oxygen, an oxidation reaction of the carbon fraction may be inhibited, so that it is possible to enhance the yield. In order to obtain such an atmosphere, for example, the atmosphere may be substituted with an inert gas such as a nitrogen gas, an argon gas or a carbon dioxide gas; the explosion chamber may be evacuated to about −0.1 to −0.01 MPaG (the symbol "G" put after the pressure unit expresses a gauge pressure; hereinafter the same); or after evacuating to release the air (oxygen), the above-described inert gas may be charged to a weak positive pressure of about +0.000 to +0.001 MPaG. The chamber is not limited to a metal-made chamber but may be, for example, a concrete-made one. In addition, the detonation may be performed in the inside of an earthwork or gallery provided by excavating the underground, without using a chamber.

In addition, it is preferred to dispose a coolant in the periphery of the raw material substance and the explosive substance within the explosion chamber because the formed diamond may be quenched to prevent phase transition to graphite carbon from occurring. In order to dispose a coolant as above, for example, the molded body or the explosion container 20 may be disposed within a cooling container 30, followed by charging a coolant 32 in a gap between the cooling container 30 and the molded body or the explosion container 20. Here, in the case where the coolant 32 is a substance which does not substantially produce an oxidative substance such as oxygen and ozone, it may inhibit an oxidation reaction of the carbon fraction, and hence, the yield may be enhanced. In order to obtain such a coolant, for example, an oxygen gas dissolved in the coolant 32 may be removed, or the coolant 32 which does not contain a constituent element producing an oxidative substance such as oxygen and ozone may be used. Examples of the coolant 32 include water and a halogenated alkyl (for example, fluorocarbons or carbon tetrachloride), and water is especially preferred because it does not substantially adversely affect the environment.

Though the explosive substance 12 is generally blasted by using a detonator or a detonating cord, in order to more surely cause a detonation, a booster (for example, Composition C-4, Composition C-4, SEP manufactured by Asahi Kasei Chemicals Corporation, etc.) may be allowed to intervene between the explosive substance 12 and the detonator or detonating cord. In this case, after installing a booster 22 and a detonator or detonating cord 24 in the molded body or the explosive container 20, for example, they are packed within the explosion chamber. In the case of using the coolant 32, it is preferred that the molded body or the explosion container 20 is housed in a fluid-tight container (for example, a bag made of, as a raw material, an olefin-based synthetic resin such as polyethylene or polypropylene) such that, for example, the coolant 32 does not penetrate into the explosion container 20. After setting up in this way, when the explosive substance 12 is blasted to underact detonation, carbon particles containing graphite carbon and diamond can be obtained as a residue thereof.

In the production method of the present invention, the residue obtained in the detonation step possibly contains, as impurities, blasted wreckage, such as a wreck of the container, a lead wire or a wire, etc. In such a case, it is preferred to provide a step of removing the wreckage from the residue obtained in the detonation step to recover the carbon particles. In this recovery step, for example, when a classification/purification treatment is performed, the carbon particles may be obtained in a form of dry powder having a desired particle diameter.

Typically, first of all, after removing rough wreckage from the obtained residue, the resultant is classified with a sieve or the like and separated into a sieve-passing material and a residue on the sieve, and the sieve-passing material is then recovered. The residue on the sieve is crushed and then again classified. Water is separated from the finally obtained sieve-passing material to prepare a dry powder. Here, the sieve-passing material through a sieve having an opening corresponding to a desired particle diameter may be prepared as a product by properly adjusting an opening of the sieve and repeating the classification/purification treatment.

In more detail, for example, in the case of performing the detonation within the explosion chamber while using water as the coolant 32, the water containing the residue is recovered, followed by sedimentation and separation. After removing rough wreckage, a supernatant is recovered as a waste fluid, and a precipitate is classified with a sieve or the like, thereby obtaining a sieve-passing material. The formed carbon fraction includes one attaching to the wreckage, and therefore, the residue on the sieve is crushed and separated by means of ultrasonic vibration or the like and then again classified with a sieve or the like. In general, since the residue on the sieve of about 30 μm is mostly blasted wreckage, such as a wreck of the explosion container 20, a lead wire or a wire, etc., it is preferred, after recovery, to be disposed as an industrial waste, and a sieve-passing material of about 30 μm is recovered as a final product. In the recovered product, water is separated by means of centrifugation or the like, followed by drying, to obtain carbon particles powder having a desired particle diameter.

For example, in the case of using an acrylic resin container as the explosion container 20, the acrylic resin is possibly contaminated. In this case, the acrylic resin may be removed by, for example, subjecting the acrylic resin to an elution treatment with acetone.

In addition, when a metal such as iron is contaminated, there may be an undesired case depending upon an application. In such a case, the metal such as iron may be removed by, for example, a treatment with hot concentrated nitric acid.

The obtained powder is a nano-scale carbon particle containing, in addition to nanodiamond, a lot of graphite carbon. However, it may be required to make good use of excellent properties of the diamond depending upon an application.

<<Carbon Particles>>

The carbon particles of the present invention are obtained by the above-described production method, and when a mass of the graphite carbon is defined as G and a mass of the diamond is defined as D, their mass ratio G/D is 2.5 or more. The composition and physical properties characterizing the carbon particles of the present invention are hereunder described in detail.

First of all, the carbon particles of the present invention can be prescribed by a content proportion of the carbon component in terms of a mass ratio. The carbon particles is formed in a manner that the raw material substance causes detonation to be decomposed to an atomic level and a carbon atom liberated therefrom without being oxidized aggregates in a solid state. During detonation, the raw material substance is in a high-temperature high-pressure state due to a decomposition reaction however, it is immediately expanded and cooled. A process from this high-temperature high-pressure state to the reduced-pressure cooling is caused within a very short time as compared with usual combustion or deflagration that is an explosion phenomenon slower than detonation, and hence, there is no time when the aggregated carbon largely grows, whereby the nano-scale carbon particles are formed.

In the case where a typical high-performance high explosive which is known to cause detonation, such as RDX or HMX as described above, is used as the raw material substance, the pressure during the detonation becomes very high, and hence, as is easily anticipated from a thermodynamic equilibrium phase diagram of carbon, the formed carbon particles contain a lot of nanodiamond.

On the other hand, in the case where a raw material substance that is not a high-performance high explosive is used, since the pressure during the detonation does not become high, synthesis of diamond is not achieved but a nano-scale carbon particle other than diamond is formed. This carbon particle contains a lot of nano-scale graphite carbon (hereinafter referred to as "nanographite").

In consequence, a content proportion of the nanodiamond and the nanographite may be controlled by the pressure during detonation of the raw material substance. That is, by using a raw material substance that is not a high-performance high explosive, the content proportion of the nanographite may be increased. However, when the pressure during detonation of the raw material substance is lower than that in the high-performance high explosive, there is a possibility of occurrence of a phenomenon in which it may be difficult to detonate the raw material substance, or even if detonation can be performed, it may be interrupted on the way. That is, this matter means that it is difficult to stably detonate the raw material substance alone. Therefore, in the case where the pressure during detonation of the raw material substance is low, it is necessary to contrive to dispose an explosive substance capable of causing detonation in the periphery of the raw material substance, thereby allowing the raw material substance to surely cause detonation. In addition, in all of the cases, it is important to choose the raw material substance having such a composition that the liberated carbon is not oxidized.

Furthermore, it is desired to remove an oxidative substance such as an oxygen gas or ozone, which oxidizes liberated carbon to form a gas of CO, $CO_2$, or the like, from the detonation system as far as possible.

In addition, in the case of detonating a low explosive or a raw material substance containing an aromatic compound having not more than 2 nitro groups, it may be presumed that all kinds of nano-scale carbon particles, such as diamond, graphite, fine carbon nanotubes and fullerenes, are formed.

From literatures (Satoshi Tomita et al., "Diamond nanoparticles to carbon onions transformation: X-ray diffraction studies", Carbon 40, pp. 1469-1474 (2002); Dilip K. Singh, et al, "Diameter dependence of interwall separation and strain in multiwalled carbon nanotubes probed by X-ray diffraction and Raman scattering studies", Diamond & Related Materials 19, pp. 1281-1288(2010); and the like) and the results of X-ray diffraction data of detonation nanodiamond acquired up to date, as described below, it may be presumed that a peak in which a diffraction angle 2θ of the X-ray diffraction data measured by a Cu(Kα) tube is near 24 to 26° (hereinafter referred to as "peak near 26°") is originated from a nanocarbon substance composed mainly of a laminate sp$^2$ carbon structure. In addition, with respect to (multi) carbon nanotubes of two layers, three layers or the like, a peak appears in this region.

Figure 2:
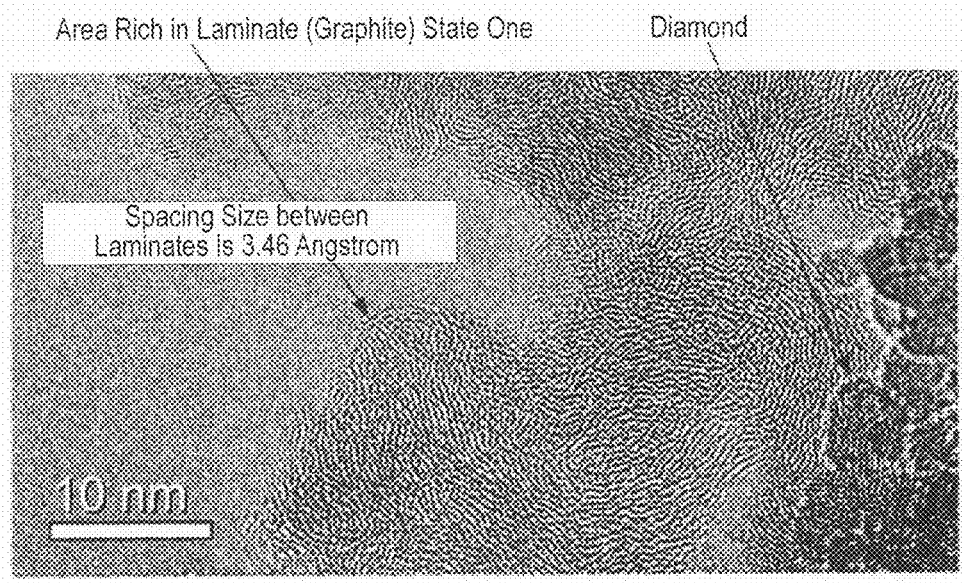
FIG. 2 is a transmission electron microscopic (TEM) photograph of carbon particles obtained in Example 3.

The results of observation of a lattice image of a transmission electron microscopic (TEM) photograph of carbon particles as described later are shown in FIG. 2. In FIG. 2, two kinds of shapes of lattice images including a round spherical shaped one and a laminate (graphite) state one were observed. Both of them are of a nano scale, and in view of the existent amounts thereof, the both are considered to be a particle of carbon as a main component. Since the particles of carbon as observed herein are anticipated to be nanodiamond and graphite carbon, their lattice spacing and spacing of the laminate were measured and compared. As for a scale bar (5 nm and 10 nm) and a magnification of TEM, a sample in which an SiGe multilayered film is attached to an Si single crystal is used as a standard sample, and at a high magnification, calibration is made on the basis of a spacing of 3.1355 angstrom of the Si111 plane. This calibration operation is confirmed to be within 5% according to an accuracy management of every month.

In the diamond in the same field of view in FIG. 2, the D 111 plane was observed, and the measurement result of the lattice spacing thereof was 2.11 angstrom. In general, the lattice spacing of the D 111 plane is said to be 2.06 angstrom, and a ratio of a difference therebetween is 2.4%. Meanwhile, the measurement result of the spacing of the observed laminate was 3.46 angstrom. A 002 spacing of a laminate of hexagonal system graphite (powder diffractometry) is said to be 3.37 angstrom, and a ratio of a difference therebetween is similarly 2.4%. Therefore, the spacing of the observed laminate and the spacing of the laminate of graphite substantially coincided with each other. In consequence, it is considered that this laminated nano-scale carbon particle is graphite carbon (nanographite) and occupies a major proportion of the carbon particles.

According to the X-ray diffraction data, though the nanodiamond can be confirmed, with respect to the nano-scale carbon particles, it is not clear what kinds of substances are contained other than the nanographite and fine multi carbon nanotubes, which bring a peak near 26°. Fine single-layered (single) carbon nanotubes and various fullerenes do not participate in the peak near 26°, and hence, the quantitative results by the peak near 26° do not include the formation amount thereof. Furthermore, it is anticipated that nano-scale carbon particles in which the laminate (graphite) structure is changed to, for example, a turbostratic structure by the detonation are also included in the peak near 26°. It may not be denied that a mixed peak of these deformed nano-scale carbon particles acts towards enlargement of the peak width near 26°.

However, it is noted from the TEM photograph that the formation amount of the fine single-layered (single) carbon nanotubes, various fullerenes, and the like are low. That is, in the case of producing carbon particles by the detonation method, it is anticipated that the formation amount of nano-scale carbon particles not expressed by the peak near 26° falls within the range of a proportion of a certain low mass ratio, and hence, it is anticipated that even if all of carbons other than diamond are presumed to be graphite carbon, there is no large error. In addition, it is presumed that carbons of other structures are scarce.

From the foregoing background, so far as the production method is specified to determine the kind, amount and constitution of each of the raw material substance and the liquid explosive substance, it is anticipated that the nanodiamond and the nanographite produced on the basis of this production method fall within a proportion of a mass ratio of a certain range. Therefore, it is anticipated that even if all of carbons other than diamond are presumed to be graphite carbon, there is no large error. For that reason, since it is presumed that carbons of other structures than the diamond and the graphite carbon are scarce, the carbon other than diamond was presumed to be graphite carbon, and its proportion was determined.

From the foregoing background, in the present invention, the carbon particles were prescribed in view of the characteristic feature that they contain graphite carbon and diamond, and have a high content proportion of the graphite carbon as compared with conventional products (the case of using a high explosive raw material). Specifically, when a mass of the graphite carbon is defined as G and a mass of the diamond is defined as D, their mass ratio G/D is 2.5 or more, preferably 3 or more, more preferably 3.5 or more, and still more preferably 4 or more. Though an upper limit of the mass ratio G/D is not particularly limited, taking into consideration the fact that the diamond is contained, it is preferably 100 or less, more preferably 50 or less and still more preferably 20 or less.

The mass ratio G/D is one determined by the method described in the Examples as described below.

Since the carbon particles of the present invention contain graphite carbon and diamond, they are useful for applications such as a tool, an anti-wear agent and a lubricating agent, while making good use of excellent properties of diamond, such as polishing properties, durability and wear resistance. In addition, they are useful for applications such as a fiber material, a resin coating of imparting functionality, a drug delivery system, an electronic element cover, an electrode material of battery, a conductive film, a reinforced rubber or water-repellent rubber, a catalyst, and an adsorbing agent, while making good use of excellent properties of graphite carbon, such as conductivity, water repellency and biocompatibility.

EXAMPLES

The present invention is hereunder more specifically described by reference to Examples, but it should be construed that the present invention is not limited by the following Examples at all. It is possible to carry out the present invention by making suitably modifications within the scope capable of being adapted with the gist described previously or later, and these are included in the technical scope of the present invention.

First of all, the methods of evaluating the carbon particles of the present invention are described.

<XRD Quantitative Method>

From the measurement results of X-ray diffraction (XRD), with respect of a diffraction peak in the (220) plane of diamond appearing near 2θ=75°, an integrated intensity was determined, and a content proportion of the diamond was determined by using each of previously prepared calibration curves.

Diamond which had been purified by removing graphite carbon and be like, with perchloric acid, from carbon particles containing diamond as separately produced by the present invention, was used as a standard substance for determination of the quantity of diamond.

A silicon powder (manufactured by Osaka Yakken Co., Ltd., Stansil-G03A, D50 =5.2 µm) in an amount of 10 mass % relative to the whole amount of carbon was added as an internal standard.

As for the calibration curve, 5 standard samples were used, and 4 points were measured from the ratio of an integrated intensity of the above-described diffraction peak and an integrated intensity of the diffraction peak on each of the (220) plane and the (311) plane of a silicon crystal added to each of the samples, thereby preparing one for diamond. The reason why the two peaks of the silicon crystal were used resides in the matter of suppressing any influence of orientation of the powdered silicon.

The 5 standard samples are those in which the silicon crystal was mixed such that the amount of diamond is 0 mass %, 25 mass %, 50 mass %, 75 mass %, and 100 mass %.

Figure 5:
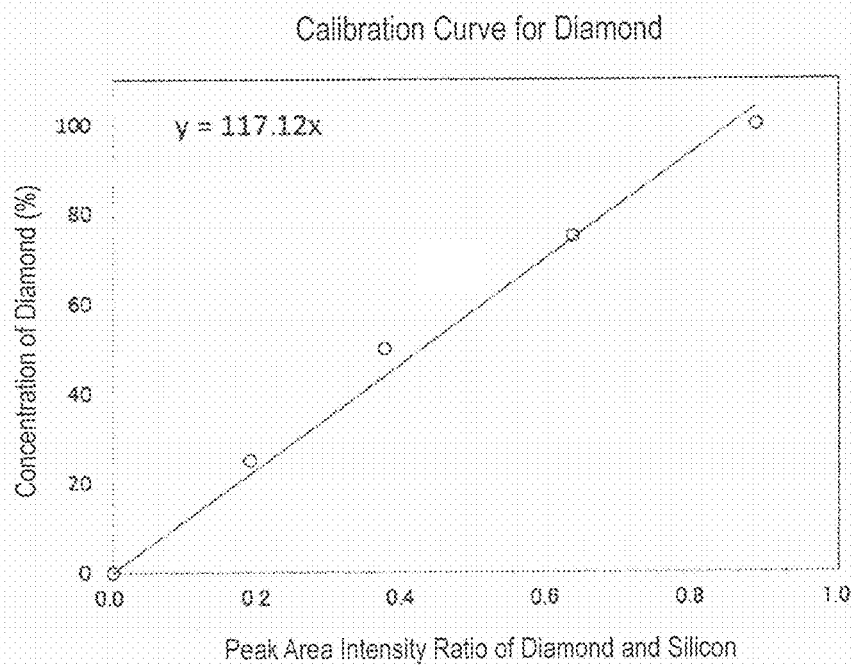
FIG. 5 is a graph showing a calibration curve used in determining a diamond content proportion of carbon particles.

The calibration curve for diamond was obtained by plotting a concentration of diamond on the ordinate and a peak area intensity ratio D220/(Si220+Si311) of diamond and silicon on the abscissa, respectively. A relational expression between the concentration Y and the intensity ratio X through collinear approximation by the least squares method was Y=117.1X. The obtained calibration curve is shown in FIG. 5.

A mass ratio G/D was calculated by dividing the obtained diamond content proportion by the estimated graphite content proportion. It was noted that diamond and graphite carbon were the main components. Any carbon of other structure was not explicitly observed.

The measurement conditions of the X-ray diffraction are shown below.
  Device name of X-ray diffraction device: Horizontal X-ray diffraction device, SmartLab, manufactured by Rigaku Corporation
  Measurement method: θ-2θ
  X-ray source: Cu-Kα ray
  Excitation voltage-current: 45 kV-200 mA
  Divergence slit: 2/3°
  Scattering slit: 2/3°
  Receiving slit' 0 6 mm <Transmission Electron Microscopic Observation>

From the measurement results with a transmission electron microscope (TEM), the carbon particles obtained by the production method of the present invention were observed to be nano-scale diamond and graphite. Therefore, TEM having a CCD camera and a photographing magnification capable of observing lattice images of diamond and graphite having a laminated structure was used. The measurement conditions of TEM are shown below.
  Device name of TEM: Transmission electron microscope, JEM-ARM200F, manufactured by JEOL Ltd.
  Measurement method: Suspension method (dispersion solvent: methanol)
  Accelerating voltage: 200 kV
  CCD camera: UltraScan, manufactured by Gatan
  Photographing magnification: 300,000 times and 800,000 times
  Imaging magnification: 2,200,000 times and 5,900,000 times (in the case of printing in A4 size)

Next, Experimental Examples of producing carbon particles by the production method of the present invention are described.

Experimental Example 1

In this Experimental Example, carbon particles were produced by the detonation method by using dinitrotoluene (DNT) as a raw material substance and using a hydrazine-based liquid high explosive as an explosive substance.

First of all, DNT (industrial grade) was melt loaded and molded in a columnar shape of a diameter of 10 cm and a height of 48 cm. The obtained molded body had a mass of 5.52 kg and a density of 1.46 g/cm$^3$. In addition, a 75% hydrazine hydrate solution of 2.50 kg of hydrazine nitrate was subdivided and prepared.

Subsequently, a detonation reaction was performed by using the explosive device as illustrated in FIG. 1. The above-described molded body as the raw material substance 10 was placed in the center of the explosion container 20 having an inside diameter of 12cm and a height of 50 cm, and the above-described liquid high explosive as the explosive substance 12 was charged in the periphery thereof. The booster 22 (SEP), a detonating cord and the No. 6 electric detonator 24 were installed in a top of the explosion container 20, followed by capping and housing in a fluid-tight polyethylene bag. A container having a capacity of 100 L was used as the cooling container 30. The explosion container 20 was placed within the cooling container 30. Here, an iron-made stand 34 and an iron-made perforated disk 36 were used and adjusted such that an outer bottom surface of the explosion container 20 was positioned in a height of 15 cm from an inner bottom surface of the cooling container 30. Then, 120 L of distilled water was charged as the coolant 32 in the cooling container 30 and the polyethylene bag, whereby the coolant 32 was charged in the gap between the cooling container 30 and the explosion container 20. After capping, the resultant was suspended in an explosion chamber having an internal volume of 30 m$^3$ from a ceiling thereof by using a wire sling. The inside of the explosion chamber was evacuated from the atmospheric pressure, thereby controlling an amount (calculated value) of an oxygen gas remaining inside the chamber to 279.9 g.

After setting up in this way, the detonating cord was blasted by the detonator, thereby detonating the explosive substance 12. Then, about 120 L of water containing a residue was recovered from the inside of the chamber, followed by sedimentation and separation to remove the rough wreckage. Here, since a supernatant was strongly alkaline, a pH thereof was made weakly acidic by adding citric acid. The weakly acidic supernatant was recovered as a waste fluid as it was. A precipitate was classified with a sieve having an opening of 100 μm/16 μm by using a vibration sieve device ("KG-700-2W", manufactured by Kowa Kogyosho Co., Ltd.). A 16 μm-sieve-passing material was recovered as it was. A residue on the sieve was crushed for about 5 minutes by an ultrasonic vibration device ("4G-250-3-TSA", manufactured by Crest), and a carbon fraction was separated from the wreckage surface and again classified with a sieve having an opening of 100 μm/32 μm/16 μm by using a vibration sieve device ("KG-700-2W", manufactured by Kowa Kogyosho Co., Ltd.), followed by recovering a sieve-passing material. Each of the sieve-passing materials was allowed to stand within a drying machine at 80° C. ("OF-450S", manufactured by AS ONE Corporation) for 24 hours to evaporate moisture, followed by preparing as a dry powder.

There were thus obtained 2,048 g in total of carbon particles including 584 g of a 16 μm-sieve-passing material, 907 g of a 32 μm-sieve-passing material and 557 g of a 100 μm-sieve-passing material. The experiment contents and the recovery amount and yield of the carbon particles in this Experimental Example are shown in the following Table 2.

Experimental Example 2

In this Experimental Example, carbon particles (2,334 g in total) including 534 g of a 16 μm-sieve-passing material, 1,315 g of a 32 μm-sieve-passing material and 485 g of a 100 μm-sieve-passing material were obtained in the same manner as in Experimental Example 1, except for changing the use amount of the hydrazine-based liquid high explosive as the explosive substance from 2.50 kg to 2.49 kg, changing the container having a capacity of 100 L as the cooling container to a container having a capacity of 200 L, and changing the use amount of distilled water as the coolant from 120 L to 220 L. The experiment contents and the recovery amount and yield of the carbon particles in this Experimental Example are shown in the following Table 2.

Experimental Example 3

In this Experimental Example, carbon particles (1,645 g in total) including 164 g of a 16 μm-sieve-passing material, 801 g of a 32 μm-sieve-passing material and 680 g of a 100 μm-sieve-passing material were obtained in the same manner as in Experimental Example 1, except for changing the use amount of DNT as the raw material substance from 5.52 kg to 5.46 g, changing the container having a capacity of 100 L as the cooling container to a container having a capacity of 200 L, changing the use amount of distilled water as the coolant from 120 L to 220 L, and controlling the amount (calculated value) of the oxygen gas remaining inside the chamber from 279.9 g to 191.0 g. The experiment contents and the recovery amount and yield of the carbon particles in this Experimental Example are shown in the following Table 2.

Figure 3:
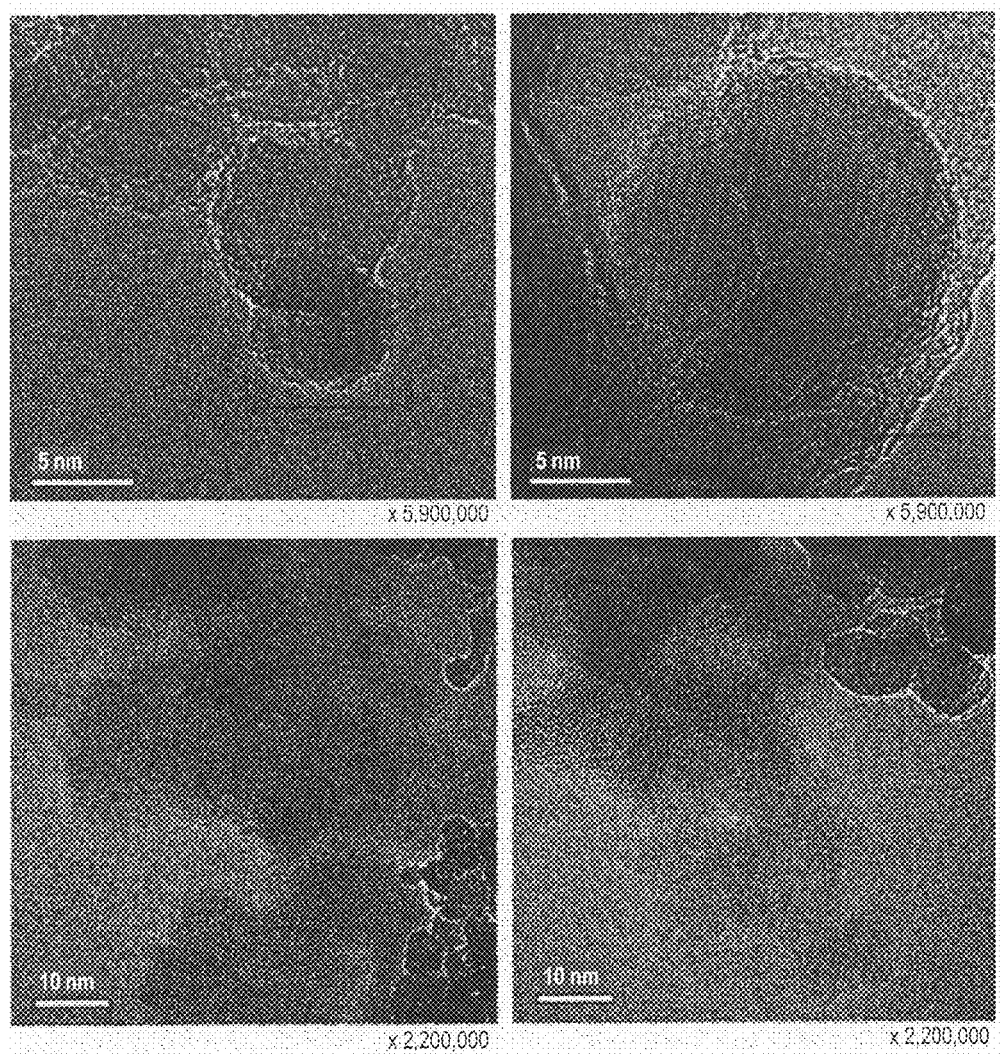
FIG. 3 is each of transmission electron microscopic (TEM) photographs of carbon particles obtained in Example 3.
Figure 4:
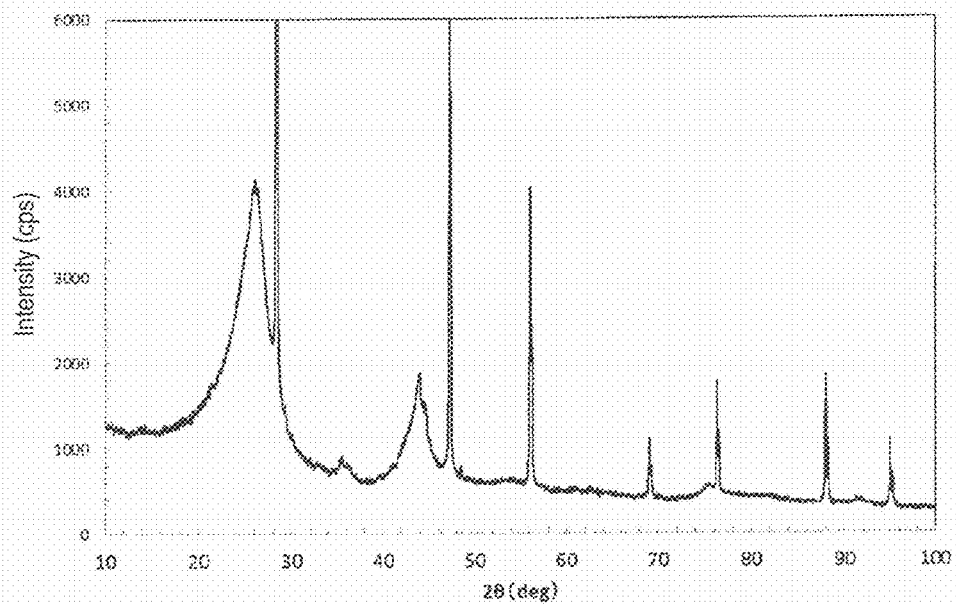
FIG. 4 is an X-ray diffraction chart of carbon particles obtained in Example 3.

Among the obtained carbon particles, a transmission electron microscopic (TEM) photograph of the 16 μm-sieve-passing material is shown in FIG. 3, and an X-ray diffraction chart of the 100 μm-sieve-passing material is shown in FIG. 4. From FIG. 3, a carbon particle having a particle diameter of about 7.0 nm (upper-left photograph) and a carbon particle having a particle diameter of about 17.5 nm (upper-right photograph) can be observed.

TABLE 2

|  |  | Experimental Example 1 (2#12) | Experimental Example 2 (2#13) | Experimental Example 3 (3#6) |
|---|---|---|---|---|
| Raw Material Substance | Kind | DNT | DNT | DNT |
|  | Mass (kg) | 5.52 | 5.52 | 5.46 |
|  | Volume (cm$^3$) | 3770 | 3770 | 3750 |
|  | Density (g/cm$^3$) | 1.46 | 1.46 | 1.46 |

TABLE 2-continued

|  |  | Experimental Example 1 (2#12) | Experimental Example 2 (2#13) | Experimental Example 3 (3#6) |
|---|---|---|---|---|
| Explosive Substance | Kind | NH + HH [1] | NH + HH [1] | NH + HH [1] |
|  | Mass (kg) | 2.50 | 2.49 | 2.50 |
| Cooling Container | Capacity (L) | 100 | 200 | 200 |
| Coolant | Volume (L) | 120 | 220 | 220 |
| Explosion Chamber | Internal Volume (m$^3$) | 30 | 30 | 30 |
|  | Amount of Residual Oxygen Gas (g) | 279.9 | 279.9 | 191.0 |
| Carbon Particles | 16 μm-Sieve-Passing Material (g) | 584 | 534 | 164 |
|  | 32 μm-Sieve-Passing Material (g) | 907 | 1315 | 801 |
|  | 100 μm-Sieve-Passing Material (g) | 557 | 485 | 680 |
|  | Recovery Amount in Total (g) | 2048 | 2334 | 1645 |
|  | Yield (%) [2] | 37.1 | 42.3 | 30.1 |

[1] Hydrazine-based liquid high explosive obtained by mixing hydrazine nitrate ($H_2N$—$NH_2 \cdot HNO_3$) and hydrazine hydrate ($H_2N$—$NH_2 \cdot H_2O$) in a mass ratio of 3:1
[2] Yield (%) = 100 × (Total recovery amount (g) of carbon particles/Mass (kg) of raw material substance × 1000)

Among the carbon particles obtained in Experimental Examples 1 to 3, with respect to the 16 μm-sieve-passing materials, the content proportion (D: provided that the carbon particles are 100 mass %) of diamond in the carbon particles was determined by the XRD quantitative method as described above, and on the assumption that the content proportion (G) of graphite carbon was carbon particles other than diamond, a mass ratio G/D was calculated therefrom. The results are shown in the following Table 3(a). In addition, the results of comparison in the mass ratio G/D with other commercially available products are shown in the following Table 3(b).

TABLE 3(a)

|  | Raw Material Substance |  |  | Carbon Particles |  | Diamond (D) | Graphite Carbon (G) |  |
|---|---|---|---|---|---|---|---|---|
|  | Kind | Mass (kg) | Explosive Substance | Recovery Amount (g) | Yield[3] (%) | Content Proportion (wt %) | Content Proportion (wt %) | Mass Ratio G/D |
| Experimental Example 1 (2#12) | DNT | 5.52 | NH + HH[2] | 2048 | 37.1 | 10.5 | 89.5 | 8.52 |
| Experimental Example 2 (2#13) | DNT | 5.52 | NH + HH[2] | 2334 | 42.3 | 8.2 | 91.8 | 11.20 |
| Experimental Example 3 (3#6) | DNT | 5.46 | NH + HH[2] | 1645 | 30.1 | 19.0 | 81.0 | 4.26 |

[1] Data in the case of using TNT alone as described in Table 2 of NPL 1
[2] Hydrazine-based liquid high explosive obtained by mixing hydrazine nitrate ($H_2N$—$NH_2 \cdot HNO_3$) and hydrazine hydrate ($H_2N$—$NH_2 \cdot H_2O$) in a mass ratio of 3:1
[3] Yield (%) = 100 × (Recovery amount (g) of carbon particles/Mass (kg) of raw material substance × 1000)

TABLE 3(b)

| Nanocarbon Particles | | Mass Ratio G/D | G/(G + D) |
|---|---|---|---|
| Experimental Example 1 (2#12) | | 8.52 | 0.90 |
| Experimental Example 2 (2#13) | | 11.20 | 0.92 |
| Experimental Example 3 (3#6) | | 4.26 | 0.81 |
| Commercially | NUAC | 2.03 | 0.67 |
| Available Product [1] | ND62 | <0.01 | <0.01 |
| (Reference) | Nanoamand ® | <0.01 | <0.01 |
| | BD | 0.16 | 0.14 |
| | UDD | 0.03 | 0.03 |

[1] BD and UDD are manufactured in Russia/Ukraine; NUAC and ND62 are manufactured in China; and Nanoamand is manufactured in Japan.

It is noted from Table 3(a) that even by using DNT that is an inexpensive non-low explosive raw material as the raw material substance or using a liquid high explosive as the explosive substance, the nanodiamond can be synthesized by the detonation method. Moreover, according to the production method of the present invention, it is noted that the content proportion of the nanodiamond is enhanced as compared with a conventional case using the low-explosive raw material (for example, TNT) alone (the case of using TNT alone as described in Table 2 of NPL 1).

It is said that the crystallite size can be determined from the X-ray diffraction data according to the Scherrer equation: $D = K\lambda / \beta \cos\theta$. Here, D is a crystallite size (angstrom); $\lambda$ is a wavelength of an X-ray tube (in the Examples, 1.5418 angstrom of the Cu-K$\alpha$ ray); $\beta$ is an enlargement of the diffraction X-rays by the crystallite; $\theta$ is a diffraction angle (rad); and K is a Scherrer constant and was defined as 0.9 (B. D. Cullity (author), Gentaro Matsumura (translator), "Elements of X Ray Diffraction—Primary Source Edition", Agne Shofu, March 1999). $\beta$ determined from $\beta = (\beta_{exp}^2 - \beta_i^2)^{1/2}$ by using a width $\beta$ exp of actually measured diffraction X-rays and an enlargement $\beta$i of diffraction X-rays by the device.

As for the actually measured diffraction X-rays, after performing smoothening, background removal and K$\alpha$2 removal, a half-value width of each of a peak near 26° (generally named G002) and a peak near 43° (generally named D111) was determined, and this was defined as the width $\beta$ exp of diffraction X-rays. In addition, 10 mass % of an Si powder (manufactured by Osaka Yakken Co., Ltd., StanSil-G03A, a central particle diameter 5.2 μm) was added, and a half-value width of a peak near 47° of diffraction X-ray (generally named Si220) was defined as $\beta$i. As the X-ray diffraction device, the same device of horizontal X-ray diffraction device, SmartLab, manufactured by Rigaku Corporation as described in the foregoing <XRD quantitative method> was used.

The crystallite size presumed from the X-ray diffraction data obtained by actually measuring the carbon particles obtained in Experimental Examples 1 to 3 is shown in the following Table 4. As a result, the crystallite size of diamond is considered to be 2 to 5 nm. That is, the crystallite size of diamond determined from the diffraction X-ray width of diamond according to the Scherrer equation substantially coincides with the results of TEM observation as described later.

On presuming the crystallite size by this method, it is presumed that the spacing is constant and only the crystallite size is different. However, in the graphite carbon, it is noted that though hexagonal net surfaces of graphite are laminated in parallel, the direction thereof is of a so-called turbostratic structure in which no regularity is seen. For that reason, it is anticipated that the crystallite size determined from a mixed peak near 26° in where various deformed materials participate is not accurate. Therefore, the crystallite size of graphite carbon presumed by the method is made as a reference data.

In addition, though a particle diameter of primary particles observed in the transmission electron microscopic (TEM) photograph of carbon particles as described later is approximately several to 20 nm, it is presumed that the crystallite size presumed from the X-ray diffraction data is one expressing a particle having a smallest particle diameter shown in the photograph.

TABLE 4

| | | Width of Diffraction X-Rays $\beta$exp | | Enlargement of Diffraction X-Rays | | |
|---|---|---|---|---|---|---|
| | | | | Device $\beta$i | | |
| | Classification | 2θ (°) | Half-Value Width (rad) | Half-Value Width of Si220 (rad) | Enlargement $\beta$ by Crystallite (rad) | Presumed Crystal Size (angstrom) |
| Experimental Example 1 (2#12) | G002 | 25.7 | 0.078 | 0.003 | 0.0784 | 21 |
| | D111 | 43.6 | 0.063 | | 0.0632 | 24 |
| Experimental Example 2 (2#13) | G002 | 25.8 | 0.070 | 0.003 | 0.0702 | 25 |
| | D111 | 43.6 | 0.056 | | 0.0564 | 26 |
| Experimental Example 3 (3#6) | G002 | 26.0 | 0.054 | 0.003 | 0.0538 | 39 |
| | D111 | 43.8 | 0.026 | | 0.0262 | 54 |

<<Summary of Experimental Results>>

Table 5 shows the experiment contents, the recovery amount and yield of carbon particles, the proportion of diamond and graphite carbon in carbon particles, the diamond crystallite size determined from the line width of X-ray diffraction line, and the crystallite size of diamond and graphite carbon determined approximately from the transmission electron microscopic photograph, in the present Experimental Examples 1 to 3. It was confirmed from those results that the carbon particles containing nano-size diamond and graphite carbon could be produced.

TABLE 5

| | Experiment Contents | | | Experiment Results | | | | | | |
|---|---|---|---|---|---|---|---|---|---|---|
| | Raw Material | | | Carbon Particles | | | XRD | TEM Observation Size (angstrom)[5] | | |
| | Substance | | | Recovery | | | Crystallite | Particle | | |
| | Kind | Mass (kg) | Explosive Substance | Amount (g) | Yield (%)[2] | Mass Ratio G/D[3] | Size (angstrom)[4] | Diameter of Diamond | Diamond D111 | Graphite Carbon |
| Experimental Example 1 (2#12) | DNT | 5.52 | NH + HH[1] | 2,048 | 37.1 | 6.67 | 24 | — | — | — |
| Experimental Example 2 (2#13) | DNT | 5.52 | NH + HH[1] | 2,334 | 42.3 | 8.33 | 26 | — | — | — |
| Experimental Example 3 (3#6) | DNT | 5.46 | NH + HH[1] | 1,645 | 30.1 | 4.76 | 54 | Several to Several Tens | 2.1 | 3.5 |

[1] Hydrazine-based liquid high explosive obtained by mixing hydrazine nitrate ($H_2N—NH_2 \cdot HNO_3$) and hydrazine hydrate ($H_2N—NH_2 \cdot H_2O$) in a mass ratio of 3:1; Data in the case of using TNT alone as described in Table 2 of NPL 1
[2] Yield (%) = 100 × (Recovery amount (g) of carbon particles/Mass (kg) of raw material substance × 1000)
[3] Mass ratio G/D: Mass proportion of graphite carbon (G) and diamond (D) in carbon particles
[4] XRD crystallite size: Diamond crystallite size determined from a line width of X-ray diffraction line (angstrom)
[5] TEM observation size: Primary particle diameter of diamond, lattice spacing of D111 plane of diamond and spacing of laminate of graphite carbon, each determined approximately from the transmission electron microscopic photograph (angstrom)

While the present invention has been described in detail and with reference to specific embodiments thereof, it will be apparent to one skilled in the art that various changes and modifications can be made therein without departing from the spirit and scope of the present invention.

The present application is based on a Japanese patent application (Patent Application No. 2013-273468) filed on Dec. 27, 2013, the contents of which are incorporated herein by reference.

INDUSTRIAL APPLICABILITY

The present invention makes it possible to produce carbon particles stably and at low production costs, and therefore, may make significant contributions in various fields related to applications which make good use of excellent properties thereof.

REFERENCE SIGNS LIST

10: Raw material substance
12: Explosive substance
20: Explosion container
22: Booster
24: Detonator or detonating cord
30: Cooling container
32: Coolant
34: Stand
36: Perforated disk

The invention claimed is:

1. A method for producing a carbon particle by a detonation method, comprising:
   a step of placing a raw material substance containing an aromatic compound having not more than 2 nitro groups in an explosion container;
   a step of disposing an explosive substance having a detonation velocity of 6,300 m/s or more in the periphery of the raw material substance; and
   a step of allowing the explosive substance to detonate, wherein
   the explosive substance is a liquid at a normal temperature and a normal pressure, and
   the liquid comprises at least one kind selected from the group consisting of a mixture of hydrazine and hydrazine nitrate, a mixture of hydrazine and ammonium nitrate, nitromethane, and a mixture of hydrazine and nitromethane.

2. The method according to claim 1, wherein the raw material substance comprises at least one kind selected from the group consisting of dinitrotoluene, dinitrobenzene and dinitroxylene.

3. The method according to claim 1, wherein the detonation is performed in a state where the raw material substance and the explosive substance are charged within a chamber.

4. The method according to claim 3, wherein an atmosphere within the chamber does not substantially contain an oxygen gas.

5. The method according to claim 3, wherein a coolant is disposed in the periphery of the raw material substance and the explosive substance within the chamber.

6. The method according to claim 5, wherein the coolant is a substance which does not substantially produce an oxidative substance.

7. The method according to claim 1, further comprising a step of recovering the carbon particle from a residue obtained in the detonation step.

8. The method according to claim 1, wherein when a mass of a graphite carbon is defined as G and a mass of a diamond is defined as D, their mass ratio G/D is 2.5 or more.

9. The method according to claim 1, wherein in the disposing step, the explosive substance surrounds the raw material substance while including the raw material substance.

10. The method according to claim 1, wherein the detonation velocity of the explosive substance is higher than that of the raw material substance.

11. The method according to claim 1, wherein a pressure during detonation of the explosive substance is higher than that of the raw material substance.

12. A method for producing a carbon particle by a detonation method, comprising:
    a step of placing a raw material substance containing an aromatic compound having not more than 2 nitro groups in an explosion container;

a step of disposing an explosive substance having a detonation velocity of 6,300 m/s or more in the periphery of the raw material substance; and a step of allowing the explosive substance to detonate, wherein the explosive substance is an explosive substance in which carbon is not included as a constituent element.

* * * * *